(12) United States Patent
Fu et al.

(10) Patent No.: US 10,695,135 B2
(45) Date of Patent: Jun. 30, 2020

(54) NON-INVASIVE POSITIONING SYSTEM AND METHOD FOR SCREWING AND FIXING A BONE

(71) Applicants: KAOHSIUNG MEDICAL UNIVERSITY, Kaohsiung (TW); NATIONAL SUN YAT-SEN UNIVERSITY, Kaohsiung (TW)

(72) Inventors: Yin-Chih Fu, Kaohsiung (TW); Jau-Sheng Wang, Keelung (TW); Tien-Ching Lee, Kaohsiung (TW); Mei-Ling Ho, Kaohsiung (TW); Wei-Chi Chen, Taichung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 275 days.

(21) Appl. No.: 15/805,351

(22) Filed: Nov. 7, 2017

(65) Prior Publication Data

US 2018/0125587 A1    May 10, 2018

Related U.S. Application Data

(60) Provisional application No. 62/419,410, filed on Nov. 8, 2016.

(51) Int. Cl.
*A61B 34/20* (2016.01)
*A61B 17/17* (2006.01)
*A61B 17/72* (2006.01)
*A61B 17/88* (2006.01)
(Continued)

(52) U.S. Cl.
CPC .......... *A61B 34/20* (2016.02); *A61B 17/1703* (2013.01); *A61B 17/1725* (2013.01); *A61B 17/72* (2013.01); *A61B 17/88* (2013.01); *A61B 17/8875* (2013.01); *A61B 2017/564* (2013.01);
(Continued)

(58) Field of Classification Search
CPC ... A61B 17/1725; A61B 34/20; A61B 17/164; A61B 17/1717; A61B 17/72
See application file for complete search history.

(56) References Cited

U.S. PATENT DOCUMENTS 5,417,688 A * 5/1995 Elstrom ............. A61B 17/1703
601/3
6,718,194 B2 * 4/2004 Kienzle, III ....... A61B 17/1703
378/20
(Continued)

*Primary Examiner* — Andrew Yang
(74) *Attorney, Agent, or Firm* — Hannah Tien

(57) ABSTRACT

The present invention relates to a non-invasive positioning system for screwing and fixing a bone, where a intramedullary nail is inserted to marrow of the bone, and the intramedullary nail comprises a wall and at least one through-hole through the wall for screwing and fixing by at least one corresponding set screw, the system comprises: an in vitro locator having at least one light source to emit a laser with a wavelength to the muscle tissue to form an incident light and running through the muscle tissue and the bone to form a penetrated light, an optical holder having an optical lens and a positioning ring portion for removably disposing the optical lens, wherein the focusing spot of the incident light, the focusing spot of the penetrated light, and the at least one through-hole are aligned in a line to confirm a linear position for screwing and fixing the intramedullary nail.

4 Claims, 6 Drawing Sheets

(51) Int. Cl.
*A61B 17/56* (2006.01)
*A61B 17/90* (2006.01)

(52) U.S. Cl.
CPC ... *A61B 2017/90* (2013.01); *A61B 2034/2055* (2016.02); *A61B 2034/2068* (2016.02)

(56) References Cited

U.S. PATENT DOCUMENTS 8,814,868 B2 *   8/2014   Janna ................ A61B 17/1725
                                                           606/67
2010/0030219 A1 * 2/2010  Lerner ............... A61B 17/1703
                                                           606/87

\* cited by examiner

NON-INVASIVE POSITIONING SYSTEM AND METHOD FOR SCREWING AND FIXING A BONE

CROSS-REFERENCES TO RELATED APPLICATIONS

The present application claims priority to U.S. Provisional Appl. No. 62/419,410 filed on Nov. 8, 2016, incorporated herein by reference in its entirety.

BACKGROUND OF THE INVENTION

Field of the Invention

The present invention relates to a non-invasive positioning system and method for screwing and fixing a bone, and more particularly to a technique for rapid, safe and accurate in vitro positioning using laser, which penetrates through muscle tissue, bone marrow and output via through-hole from one side of the muscle tissue to determine the precise positioning of screwing and fixing screw to the bone marrow via through-hole.

Description of Prior Art

Lower extremity fractures are one of the most common fractures in orthopedic clinical practice. The fractures often result in long-term and extensive disability, especially for multiple system injuries after high-intensity trauma. Intramedullary nail and minimally invasive interlocking bone plate are considered to be the primary fixation for treatment of long bone fractures of the lower limbs. In current techniques, although bone nail/bone plate technique of tibia and femur is well developed, distal screw fixing is still a nightmare for many orthopedic surgeons. Free-hand technique of attaining "perfect-circles" with the assistance of fluoroscopy is most common method for the insertion of distal locking screw. Its pitfalls include increased operative time, increased radiation exposure, and the incidence of screw misplacement. Further, many targeting systems and techniques have been developed, such as: drill guide extensions, computer-aided navigation systems, trans-illumination methods, distal targeting guide-lines, and other free-hand techniques, and even "nail-over" procedures by using two intramedullary nails. However, most of them are expensive, difficult-to-operate, or the error is too large to accurately locate the position of through-hole. In addition, the prior art is usually to use in vivo light positioning. Although penetration thickness of the light is thinner, there is a need to consider not only the health problems such as human body compatibility, but also the damage on human body caused by the light source. The prior art is to place light bulb or other lighting device directly into the body. It must take into account the impact of heat radiation produced by the light bulb itself on body tissue when the power of light source is too high; and the risk of damage to the light bulb caused by intramedullary body fluid.

The present invention is directed to solve the above problems by providing in vitro positioning to find through-hole and screwing and fixing the screw to the intramedullary nail, to reduce the light scattering by optical means, to be suitable for use in a variety of different brands of bone nail/bone plate, to reduce the time of operation with new positioning method, to reduce misplacement of screw, and to reduce the amount of radiation from fluoroscopy.

SUMMARY OF THE INVENTION

The present invention provides a non-invasive positioning system for screwing and fixing a rigid means for supporting a living body, i.e. a bone, where an intramedullary nail is inserted to a semi-solid tissue, i.e. marrow of the bone, and the intramedullary nail comprises a wall and at least one through-hole running through the wall for screwing and fixing by at least one corresponding set screw, the system comprises: an in vitro locator having at least one light source, in which the in vitro locator is used to make 180 degree rotation with respect to muscle tissue to observe dark area two times on two sides of the wall resulting from the through-hole running through the wall, and a middle point of the two dark areas is set as a center of the through-hole, wherein the at least one light source emits a laser with a wavelength to the muscle tissue to form an incident light and running through the muscle tissue and the bone to form a penetrated light, and brightness of the laser is adjustable; and an optical holder having an optical lens and a positioning ring portion for removably disposing the optical lens, wherein the optical lens and the positioning ring portion are used to move and determine the positioning direction of the optical holder according to focusing spot of the incident light and focusing spot of the penetrated light, wherein the focusing spot of the incident light, the focusing spot of the penetrated light, and the at least one through-hole are aligned in a line to confirm a linear position for screwing and fixing the intramedullary nail.

The present invention also provides a non-invasive positioning method for screwing and fixing a bone, comprising steps of: inserting an intramedullary nail into marrow of a fractured lower limb bone, the intramedullary nail comprising at least one through-hole for screwing and fixing; providing an in vitro locator having at least one light source for emitting a laser with a wavelength to a muscle tissue covering the lower limb bone, the in vitro locator making 180 degree rotation with respect to the muscle tissue, to search for a position to penetrate the through-hole, and fine-tuning a light spot until the brightest position after the light spot is found, wherein the at least one light source is guided by an optical fiber to emit the laser; providing a attenuation sheet such that intensity of the laser coupled to the optical fiber is dimed until easy to observe when penetrating through the muscle tissue; allowing the at least one light source to emit lasers with two wavelengths, the lasers being able to generate a center light spot with two concentric circles, to facilitate positioning of a center point; providing at least one polarizer and adjusting an included angle for passing the two lasers with a fixed direction so that penetrated lasers have a clear light spot; providing an optical holder having a focusing lens fixed to center of the light spot to observe minute light spot directly; fixing one holder of the optical holder on the two light spots of the incident light and the penetrated light, and to ensure that the two light spots, the through-holes, and a drill aligned in a same line; and cutting skin on a center spot of the penetrated light end until the bone is visible, drilling on the lower limb bone with a drill and screwing a set screw.

BRIEF DESCRIPTION OF THE DRAWINGS

FIG. 1A is a schematic diagram of a positioning system of the present invention for searching through-hole (in vitro locator). FIG. 1B is a schematic diagram of a positioning system of the present invention for screwing and fixing a screw.

DETAILED DESCRIPTION OF THE INVENTION

Figure 1A:
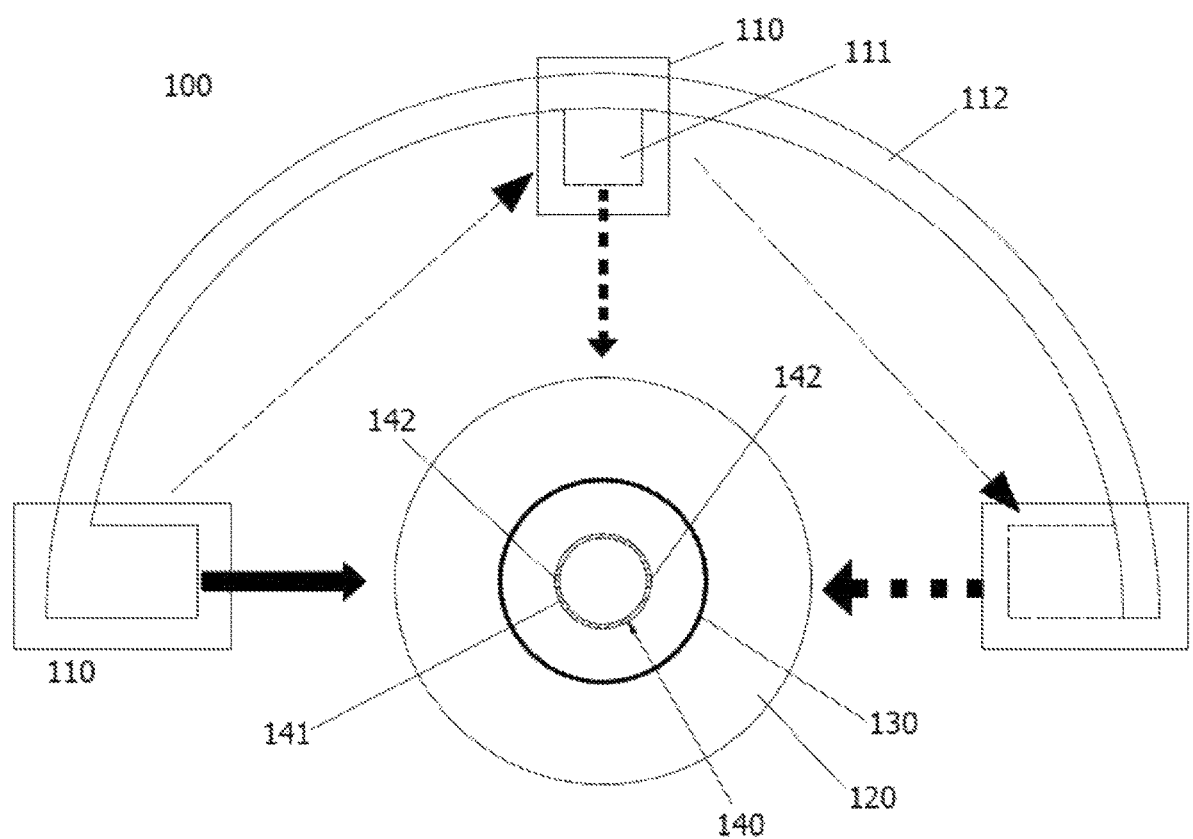
FIGS. 1A and 1B illustrate a schematic diagram of a non-invasive positioning system for screwing and fixing a bone of the present invention.

It is an object of the present invention to provide a non-invasive positioning system and method for screwing and fixing a bone to non invasively emit laser in vitro to precisely and quickly screwing and fixing a screw to intramedullary nail via through-hole.

Another object of the present invention is to provide an in vitro positioning method that increase the optical power so as to penetrate twice the thickness of the bone and soft tissue using the principle of optical fiber coupling.

A further object of the present invention is to use different wavelengths or polarized light to reduce light scattering as it penetrates the bone and soft tissue.

A still further object of the present invention is to provide a circular slide rail and to be fine-tuned positioning to quickly and correctly find the through-hole of intramedullary nail.

Given that the morphology and anatomical position of fractures in clinical practice may make the position of screw inconsistent: screw misplacement probability for nailing position and angle, a still further object of the present invention is to solve the issue of nailing position using clear light spot to be observed by optical positioning. For nailing angle, the concept of a line from two points is used, that is, the incident light and through-hole must be in a line, and the through-hole and the output light must be in a line.

The present invention discloses a non-invasive positioning system for screwing and fixing a bone, where an intramedullary nail is inserted to marrow of the bone, and the intramedullary nail comprises a wall and at least one through-hole running through the wall for screwing and fixing by at least one corresponding set screw, the system comprises: an in vitro locator having at least one light source, in which the in vitro locator is used to make 180 degree rotation with respect to muscle tissue to observe dark area two times on two sides of the wall resulting from the through-hole running through the wall, and a middle point of the two dark areas is set as a center of the through-hole, wherein the at least one light source emits a laser with a wavelength to the muscle tissue to form an incident light and running through the muscle tissue and the bone to form a penetrated light, and brightness of the laser is adjustable; and an optical holder having an optical lens and a positioning ring portion for removably disposing the optical lens, wherein the optical lens and the positioning ring portion are used to move and determine the positioning direction of the optical holder according to focusing spot of the incident light and focusing spot of the penetrated light, wherein the focusing spot of the incident light, the focusing spot of the penetrated light, and the at least one through-hole are aligned in a line to confirm a linear position for screwing and fixing the intramedullary nail.

In one embodiment, the at least one light source further comprises an optical fiber to guide emission of the laser.

In one embodiment, the positioning system further comprises a first polarizer disposed between the at least one light source and the muscle tissue, where a polarization angle is adjustable for making the incident light emitting along a fixed direction and form a light with a single vibration direction, to penetrate deeply into the muscle tissue.

In one embodiment, the positioning system further comprises an attenuation sheet disposed at a light penetrated side of the muscle tissue for reducing repetitive scattering light emitted from inner of the muscle tissue to outside of the muscle tissue and allowing straight light to go through.

In one embodiment, the positioning system further comprises a second polarizer disposed at a light penetrated side of the muscle tissue for passing the penetrated light with the fixed direction, and suppressing scattering light which is passing through the muscle tissue to interfere with external imaging.

In one embodiment, intensity I of the penetrated light passing the polarizer is calculated by $I=I_0 \cos^2 \theta$, where $I_0$ is intensity of the incident light, $\theta$ is included angle between a polarization direction and a principal axis of the incident light.

In one embodiment, the at least one light source is able to emit two lasers of different wavelengths for respectively generating a center light spot with two concentric circles to facilitate positioning of a center point.

In one embodiment, the positioning system further comprises a slide rail for placing the at least one light source for rotation.

In one embodiment, wavelengths of the two lasers are 635 nm and 1064 nm.

In one embodiment, the positioning system further comprises a fiber coupler (NX1 coupler) for combining at least two light sources which emit laser of the same wavelength to improve luminous power.

In one embodiment, wavelength of the laser is ranging from 600 nm to 1500 nm.

In one embodiment, the bone is a fractured lower limb bone.

In one embodiment, the positioning system further comprises a charge coupled device (CCD) for receiving the two center light points.

In one embodiment, the at least one light source is a light source that generates pulsed laser or a light source that controls laser emitted time interval.

The present invention also discloses a non-invasive positioning method for screwing and fixing a bone, comprising steps of: inserting an intramedullary nail into marrow of a fractured lower limb bone, the intramedullary nail comprising at least one through-hole for screwing and fixing; providing an in vitro locator having at least one light source for emitting a laser with a wavelength to a muscle tissue covering the lower limb bone, the in vitro locator making 180 degree rotation with respect to the muscle tissue to search for a position to penetrate the through-hole, and fine-tuning a light spot until the brightest position after the light spot is found, wherein the at least one light source is guided by an optical fiber to emit the laser; providing a attenuation sheet such that intensity of the laser coupled to the optical fiber is dimed until easy to observe when penetrating through the muscle tissue; allowing the at least one light source to emit lasers with two wavelengths, the lasers being able to generate a center light spot with two concentric circles, to facilitate positioning of a center point; providing at least one polarizer and adjusting an included angle for passing the two lasers with a fixed direction so that penetrated lasers have a clear light spot; providing an optical holder having a focusing lens fixed to center of the light spot to observe minute light spot directly; fixing one holder of the optical holder on the two light spots of the incident light and the penetrated light, and to ensure that the two light spots, the through-holes, and a drill aligned in a same line; and cutting skin on a center spot of the penetrated light end until the bone is visible, drilling on the lower limb bone with the drill and screwing a set screw.

In one embodiment, the positioning method further repeats the steps to position two nearer distal through-holes and two nearer proximal through-holes (proximal holes), and screwing a set screw.

In one embodiment, wavelength of the laser is ranging from 600 nm to 1500 nm.

In one embodiment, wherein wavelengths of the two lasers are 635 nm and 1064 nm.

REFERENCES NUMERALS

100: non-invasive positioning method for screwing and fixing a bone;
100a: a schematic diagram of a positioning system for searching through-hole;
100b: a schematic diagram of a positioning system for screwing and fixing a screw;
110: in vitro locator;
111,1111,1112: at least on light source;
112: slide trail;
113: optical fiber;
120: muscle tissue;
130: bone marrow;
140: intramedullary nail;
141: wall; 142: through-hole;
150: optical holder;
151: optical lens;
152: positioning ring portion;
160: first polarizer;
160': second polarizer;
170: attenuation sheet;
180: charge coupler;
190: optical fiber coupler.

Examples

The examples below are non-limiting and are merely representative of various aspects and features of the present invention.

Figure 1B:
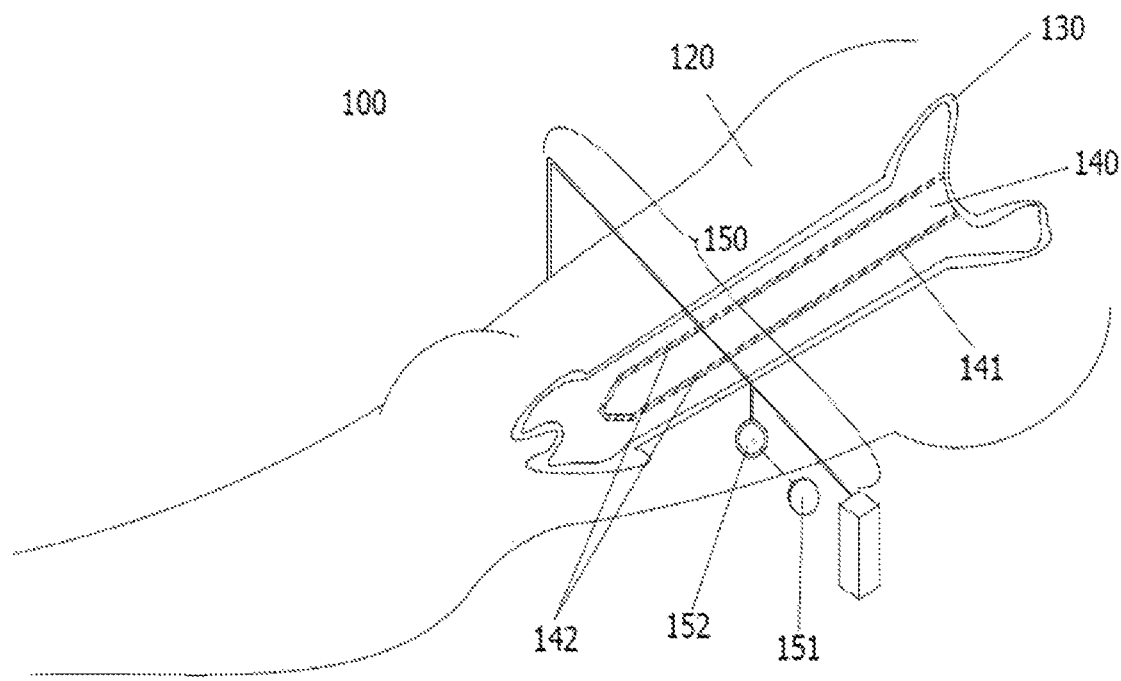

FIGS. 1A and 1B illustrate a schematic diagram of a non-invasive positioning system for screwing and fixing a bone of the present invention 100. FIG. 1A is a schematic diagram of a positioning system of the present invention for searching through-hole (in vitro locator). FIG. 1B is a schematic diagram of a positioning system of the present invention for screwing and fixing a screw. FIGS. 1A and 1B is an example of a non-invasive positioning system for screwing and fixing a bone of the present invention 100, where an intramedullary nail 140 is inserted to marrow of the bone 130, and the intramedullary nail 140 comprises a wall 141 and at least one through-hole 142 running through the wall 141 for screwing and fixing by at least one corresponding set screw (not shown), the system 100 comprises: an in vitro locator 110 having at least one light source 111, in which the in vitro locator 110 is used to make 180 degree rotation with respect to muscle tissue 120 to observe dark area two times on two sides of the wall resulting from the through-hole 142 running through the wall 141, and a middle point of the two dark areas is set as a center of the through-hole 142, wherein the at least one light source 111 emits a laser with a wavelength to the muscle tissue 120 to form an incident light and running through the muscle tissue and the bone to form a penetrated light, and brightness of the laser is adjustable; and an optical holder 150 having an optical lens 151 and a positioning ring portion for removably disposing the optical lens, wherein the optical lens and the positioning ring portion 152 are used to move and determine the positioning direction of the optical holder 150 according to focusing spot of the incident light and focusing spot of the penetrated light, wherein the focusing spot of the incident light, the focusing spot of the penetrated light, and the at least one through-hole 142 are aligned in a line to confirm a linear position for screwing and fixing the intramedullary nail 140.

Figure 2:
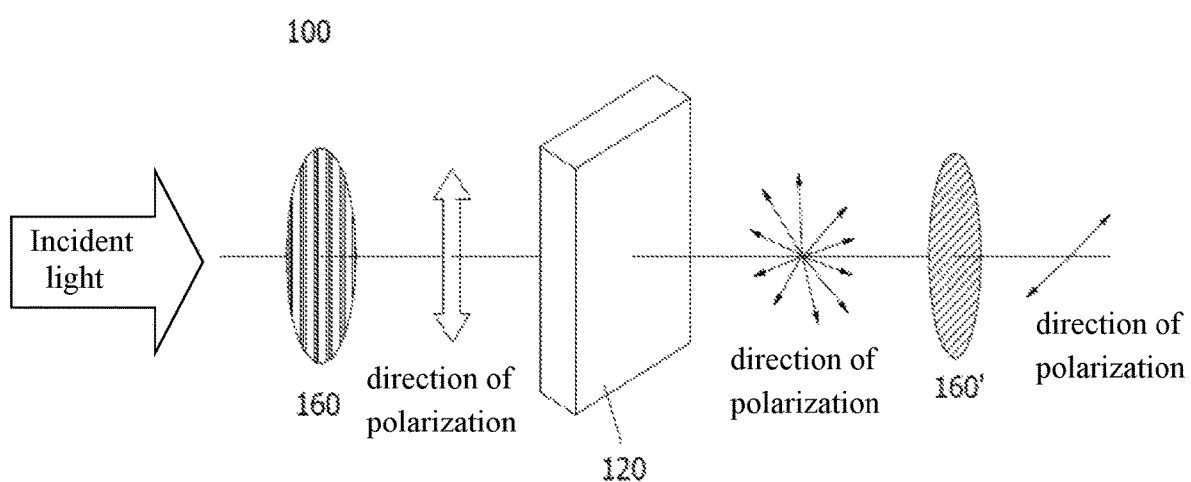
FIG. 2 illustrates a non-invasive positioning system for screwing and fixing a bone of the present invention with polarizers.

FIG. 2 illustrates a non-invasive positioning system for screwing and fixing a bone of the present invention 100 with polarizers. As shown in FIG. 2, the positioning system of the present invention 100 further comprises a first polarizer 160 disposed between the at least one light source 111 and the muscle tissue 120, where a polarization angle is adjustable for making the incident light emitting along a fixed direction and form a light with a single vibration direction, to penetrate deeply into the muscle tissue 120. The light running through the bone and soft tissue is scattered seriously and it is more difficult to find center point by in vitro observation. Therefore, the present invention uses the optical characteristics that the imaging is clearer as the incident light are increased, improving the contrast of imaging or other support methods to precisely and quickly position the center point. One way to improve is as follows:

Since the light is an electromagnetic wave, its electric field and magnetic field are interdependent to each other and vibrated perpendicular to each other. During the propagation of the photoelectron wave, the electric field (E), the magnetic field (H) and the propagation direction (K) are vertical to each other. The unpolarized light contains light vibrated in various directions. The polarizer is designed to allow only the light with a certain optical axis to pass through, thus the light passing through the polarizer will become a light with single vibration direction, which is called polarized light.

Polarized light is generated by the polarizer. As the polarized light is incident to the tissue, the light will penetrate deeply into the deeper tissue According to Malus' law: if the intensity of the incident light is $I_0$, intensity of the penetrated light is I, and included angle between a polarization direction and a principal axis of the incident light is θ, the intensity is calculated as $I=I_0 \cos^2 \theta$.

In addition, since the polarizer only allows the light in the fixed direction to passing through, the scattering light which is passing through the muscle tissue to interfere with external imaging is suppressed. The imaging light point for in vitro observation is clearer, as follows:

$$\text{Contrast} = \left| \frac{i_{tar} - i_{bg}}{i_{tar} + i_{bg}} \right|.$$

Use of polarized light can improve positioning of the center point, so that the error value is reduced. For the existing example, the error can be reduced by about 10%.

Further the present invention further comprises a second polarizer 160' disposed at a light penetrated side of the muscle tissue 120 for passing the penetrated light with the fixed direction, and suppressing scattering light which is passing through the muscle tissue 120 to interfere with external imaging. The intensity I of the penetrated light passing the polarizer 160 is calculated by $I=I_0 \cos^2 \theta$, where $I_0$ is intensity of the incident light, $\theta$ is included angle between a polarization direction and a principal axis of the incident light.

Figure 3:
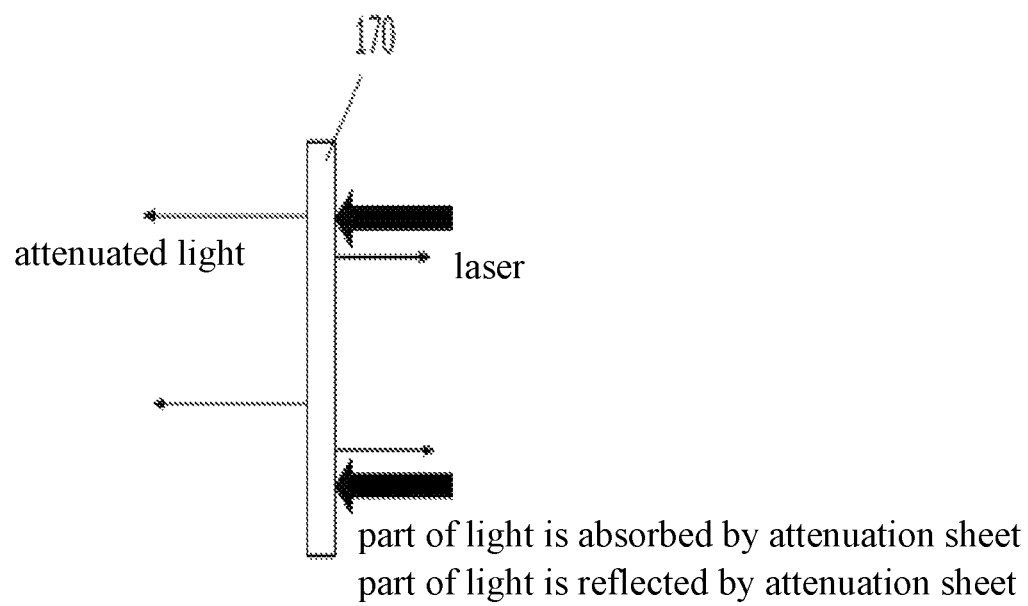
FIG. 3 illustrates a non-invasive positioning system for screwing and fixing a bone of the present invention with an attenuation sheet.

As shown in FIG. 3, the positioning system of the present invention 100 further comprises an attenuation sheet 170 disposed at a light penetrated side of the muscle tissue 120 for reducing repetitive scattering light emitted from inner of the muscle tissue to outside of the muscle tissue and allowing straight light to go through. The most accurate and effective way to observe the center point in vitro is to increase the contrast of the image. And since the intensity of light can be reduced by the attenuation sheet 170 at a constant ratio to obtain appropriate amount of light. The attenuated light does not change the spectral wavelength and the beam size, only the amount of t light is reduced. There is no effect on the color, and only luminous flux is reduced. Therefore, the inventors use the attenuation sheet or other optical component to be coupled to optical fiber, to reduce repetitive scattering light in body emitted from inner to outside. The method is easier to observe the light spot and reduce the error of positioning center point.

the light in the body to shoot in vitro, so that only the light can penetrate the organization, so that only in vitro to observe the direct light, and inhibit the scattered light out In vitro, this method can be more easily observed in vitro light points, reducing the center of the positioning error.

Further, there are different transmittances for different attenuation sheet, the suitable attenuation sheet can be selected depending on the requirements.

Figure 4:
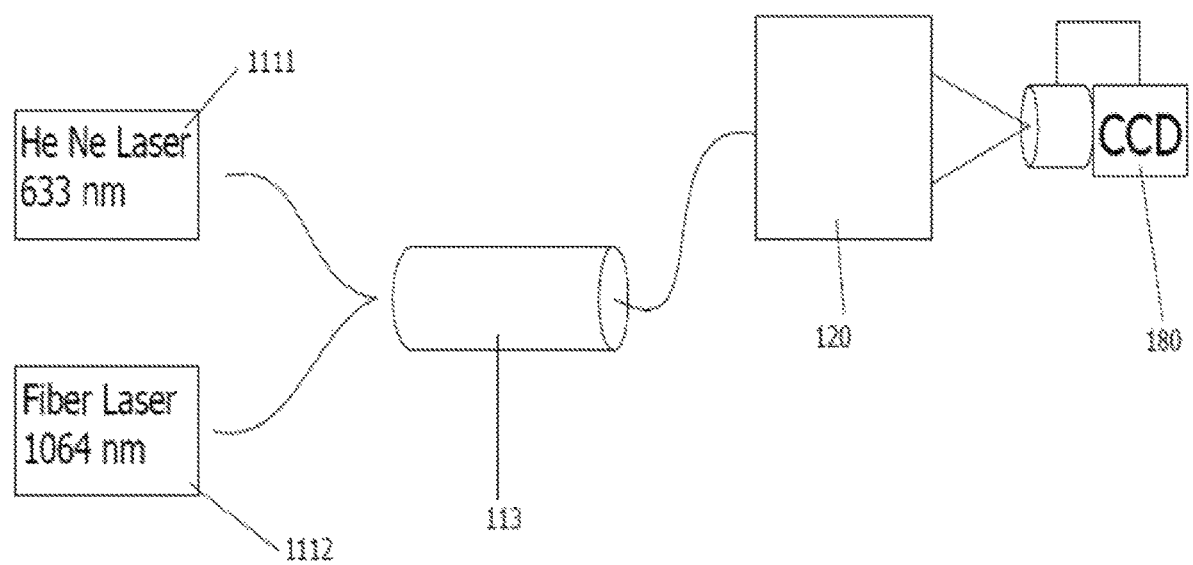
FIG. 4 illustrates a non-invasive positioning system for screwing and fixing a bone of the present invention using two light sources.

As shown in FIG. 4, in the positioning system of the present invention 100, the at least one light source can be two light sources 1111, 1112 for emitting two lasers of different wavelengths through the optical fiber 113 to an object to be measured, that is, the muscle tissue 120. As described above, there are bone marrow and intramedullary nail in the muscle tissue 120, so that respectively generating a center light spot with two concentric circles on a charge coupled device (CCD) to facilitate positioning of a center point. Two generated lasers of different wavelengths are 635 nm and 1064 nm, respectively.

Further, according to Rayleigh scattering, intensity of scattering $I(\lambda)$ is inversely proportional to the fourth power of wavelength, $$I(\lambda)_{scattering} \propto \frac{I(\lambda)_{incident}}{\lambda^4}$$

Different wavelengths will have different intensities of scattering. If two different wavelengths of light are simultaneously incident, two concentric circles are observed in vitro. It is easier to position the center point.

Figure 5:
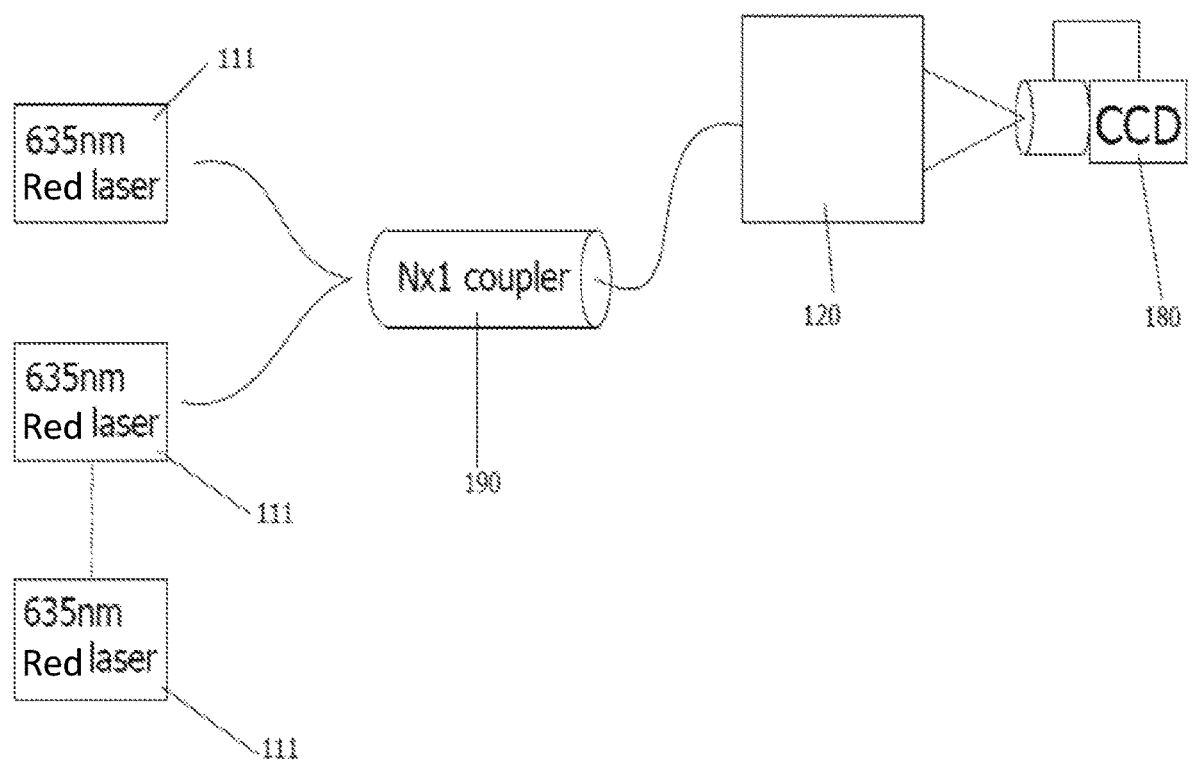
FIG. 5 illustrates a non-invasive positioning system for screwing and fixing a bone of the present invention using an optical fiber and a plurality of the same light source.

As shown in FIG. 5, the positioning system of the present invention 100 further comprises a fiber coupler (NX1 coupler) for combining at least two light sources which emit laser of the same wavelength to the object to be measured to improve luminous power. In an example of the present invention, wavelength of the laser is ranging from 635 nm.

In the positioning system of the present invention, wavelength of the laser is ranging from 600 nm to 1500 nm.

In addition, in the positioning system of the present invention, the bone is a fractured lower limb bone, and also can be applied to the upper limb bone.

According to the above-described positioning system of the present invention, another embodiment is given to explain the procedure for fixing the screw in medullary cavity for lower limb fracture as follow: 1. Preoperative preparation, including anesthesia at the fracture of the patient, cleaning, disinfection, leaving the patient on the surgical position, and manual reduction of the broken bone. 2. Cutting to the appropriate length on the appropriate part of the skin until the bone is visible, and determining the inserted position of nail on the bone. 3. Using a drilling device (reamer) or a drill (awl) to drill holes at the inserted position to open the medullary cavity. 4. Pushing the nail forward slowly to running through the fracture portion. Note that the nail should be kept in the center of the medullary cavity. 5. Using a tubular drilling device or a thinner nail to expand the medullary cavity for subsequent insertion of a fixing nail as needed.

The detailed steps of positioning of the through-hole on the nail is described below: (1) Using in vitro locator making 180 degree rotation with respect to the tissue to search for a position of the through-hole. (2) Fine-tuning a light spot until the brightest position after the light spot is found. (3) Using an attenuation sheet or other optical element such that intensity of the laser coupled to the optical fiber is dimed until easy to observe. (4) And then using the lights of different wavelengths of light to reduce light scattering in the body. (5) Adjusting an included angle of the polarizer to show linear polarized light or circular polarized light until the light spot is the clearest. The purpose of this step is to make two light spots outside the body more clear and easy to determine the position of center point. (6) Using optical lens fixed in the center of the light spot, so that doctors can observe minute light spot directly. (7) Fixing one designed holder on the two light spots, and to ensure that the two light spots, the through-holes, and a drill aligned in a same line to avoid nail misplacement. (8) Cutting skin on a center spot of the penetrated light end until the bone is visible, drilling on the lower limb bone with the drill and screwing a set screw. (9) Repeating the steps of (1) to (8) to position two nearer distal through-holes and two nearer proximal through-holes (proximal holes) and screwing a set screw.

That is, according to another example of the present invention, a non-invasive positioning method for screwing and fixing a bone of the present invention, comprising steps of: inserting an intramedullary nail into marrow of a fractured lower limb bone, the intramedullary nail comprising at least one through-hole for screwing and fixing; providing an in vitro locator having at least one light source for emitting a laser with a wavelength to a muscle tissue covering the lower limb bone, the in vitro locator making 180 degree rotation with respect to the muscle tissue, to search for a position to penetrate the through-hole, and fine-tuning a light spot until the brightest position after the light spot is found, wherein the at least one light source is guided by an optical fiber to emit the laser; providing an attenuation sheet such that intensity of the laser coupled to the optical fiber is dimed until easy to observe when penetrating through the muscle tissue; allowing the at least one light source to emit lasers with two wavelengths, the lasers being able to generate a center light spot with two concentric circles, to facilitate positioning of a center point; providing at least one polarizer and adjusting an included angle for passing the two lasers with a fixed direction so that penetrated lasers have a clear light spot; providing an optical holder having a focusing lens fixed to center of the light spot to observe minute light spot directly; fixing one holder of the optical holder on the two light spots of the incident light and the penetrated light, and to ensure that the two light spots, the through-holes, and a drill aligned in a same line; and cutting skin on a center spot of the penetrated light end until the bone is visible, drilling on the lower limb bone with a drill and screwing a set screw.

In the positioning method above, the steps are further repeated to position a near distal through-hole and a proximal through-hole (proximal hole), and screwing a set screw.

Similar to the positioning system of the present invention, wavelength of the laser of the present invention is ranging from 600 nm to 1500 nm.

In addition, wavelengths of the two lasers are 635 nm and 1064 nm.

Further, according to the present invention, the at least one light source is a light source that generates pulsed laser or a light source that controls laser emitted time interval to avoid continuous exposure to the light in the same area for a long time, and to use the time resolution to achieve increased accuracy of positioning.

What is claimed is:

1. A non-invasive positioning method for screwing and fixing a bone, comprising steps of:
    inserting an intramedullary nail into marrow of a fractured lower limb bone, the intramedullary nail comprising at least one through-hole for screwing and fixing;
    providing an in vitro locator having at least one light source for emitting a laser with a wavelength to a muscle tissue covering the lower limb bone, the in vitro locator making 180 degree rotation with respect to the muscle tissue to search for a position to penetrate the through-hole, and fine-tuning a light spot until the brightest position after the light spot is found, wherein the at least one light source is guided by an optical fiber to emit the laser;
    providing an attenuation sheet such that intensity of the laser coupled to the optical fiber is dimed until easy to observe when penetrating through the muscle tissue;
    allowing the at least one light source to emit lasers with two wavelengths, the lasers being able to generate a center light spot with two concentric circles, to facilitate positioning of a center point;
    providing at least one polarizer and adjusting an included angle for passing the two lasers with a fixed direction so that penetrated lasers have a clear light spot;
    providing an optical holder having a focusing lens fixed to center of the light spot to observe minute light spot directly;
    fixing one holder of the optical holder on the two light spots of the incident light and the penetrated light, and to ensure that the two light spots, the through-holes, and a drill aligned in a same line; and
    cutting skin on a center spot of the penetrated light end until the bone is visible, drilling on the lower limb bone with the drill and screwing a set screw.

2. The positioning method of claim 1, which further repeats the steps to position two nearer distal through-holes and two nearer proximal through-holes (proximal holes), and screwing a set screw.

3. The positioning method of claim 1, wherein wavelength of the laser is ranging from 600 nm to 1500 nm.

4. The positioning method of claim 1, wherein wavelengths of the two lasers are 635 nm and 1064 nm.

* * * * *